(12) United States Patent
Ikegami

(10) Patent No.: US 10,537,243 B2
(45) Date of Patent: Jan. 21, 2020

(54) IMAGE GENERATING APPARATUS, IMAGE GENERATING METHOD, AND COMPUTER-READABLE MEDIUM

(71) Applicant: CANON KABUSHIKI KAISHA, Tokyo (JP)

(72) Inventor: Tomoyuki Ikegami, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 100 days.

(21) Appl. No.: 15/943,887

(22) Filed: Apr. 3, 2018

(65) Prior Publication Data

US 2018/0289257 A1 Oct. 11, 2018

(30) Foreign Application Priority Data

Apr. 10, 2017 (JP) .................... 2017-077803

(51) Int. Cl.
| | | |
|---|---|---|
| *A61B 3/10* | (2006.01) | |
| *A61B 3/00* | (2006.01) | |
| *A61B 5/00* | (2006.01) | |
| *A61B 3/14* | (2006.01) | |
| *A61B 3/12* | (2006.01) | |
| *G01B 9/02* | (2006.01) | |

(52) U.S. Cl.
CPC ............ *A61B 3/102* (2013.01); *A61B 3/0025* (2013.01); *A61B 3/1225* (2013.01); *A61B 3/14* (2013.01); *A61B 5/0066* (2013.01); *G01B 9/02091* (2013.01)

(58) Field of Classification Search
CPC ......... A61B 3/102; A61B 3/0025; A61B 3/14; A61B 3/1225; A61B 5/0066; G01B 9/02091
See application file for complete search history.

(56) References Cited

U.S. PATENT DOCUMENTS 9,149,181 B2  10/2015  Matsumoto et al.
2012/0189184 A1  7/2012  Matsumoto et al.

FOREIGN PATENT DOCUMENTS

JP  2012-148003 A  8/2012

*Primary Examiner* — Jack Dinh
(74) *Attorney, Agent, or Firm* — Venable LLP

(57) ABSTRACT

Provided is an image generating apparatus including: an acquisition unit configured to acquire tomographic data on an object to be inspected, the tomographic data being obtained by performing optical coherence tomography imaging of the object to be inspected through use of measurement light; an eccentric amount acquisition unit configured to acquire an eccentric amount of an optical axis of the measurement light with respect to the object to be inspected; and a generation unit configured to generate a tomographic image through use of the acquired tomographic data. The generation unit includes: a calculation unit configured to calculate, through use of the eccentric amount, an incident angle variation of the measurement light entering the object to be inspected, and an optical path length variation of the measurement light; and a correction unit configured to correct the tomographic data through use of the incident angle variation and the optical path length variation.

15 Claims, 12 Drawing Sheets

IMAGE GENERATING APPARATUS, IMAGE GENERATING METHOD, AND COMPUTER-READABLE MEDIUM

BACKGROUND OF THE INVENTION

Field of the Invention

The present invention relates to an image generating apparatus, an image generating method, and a computer-readable medium.

Description of the Related Art

An apparatus using an optical coherence tomography (OCT) imaging method in which interference due to low coherent light is utilized (hereinafter also referred to as "OCT apparatus") is currently put into practical use. The OCT apparatus can acquire a tomographic image with resolution of about the wavelength of light entering an object to be inspected, and hence can take the tomographic image of the object to be inspected with high resolution.

In an OCT apparatus, light from a light source is split into measurement light and reference light by a beam splitter or the like. The measurement light irradiates an object to be inspected, for example, an eye, via a measurement optical path. Then, return light of the measurement light from the object to be inspected is combined with the reference light and is guided to a detector as interference light via a detection optical path. The return light described herein refers to reflected light and scattered light containing information on an interface of the object to be inspected in a direction in which the object to be inspected is irradiated with light. The interference light of the return light and the reference light is detected by the detector, and is analyzed so that the OCT apparatus can obtain a tomographic image of the object to be inspected.

When a tomographic image of a retina is taken, in general, an imaging apparatus is aligned with a center of an anterior segment to match an optical axis of the imaging apparatus with that of an eye to be inspected, and then the eye to be inspected is irradiated with measurement light by the imaging apparatus. However, there are also a large number of cases in which a peripheral portion of a pupil is irradiated with the measurement light to take a tomographic image, for example, in order to avoid opacity of a crystalline lens in a cataract eye. There is also a case in which the eye to be inspected may move unintentionally after the alignment, with the result that the optical axis of the imaging apparatus is displaced from that of the eye to be inspected. In the following, a state in which the optical axis of the imaging apparatus (measurement light) is displaced from that of the eye to be inspected (object to be inspected) refers to "there is alignment eccentricity".

When there is alignment eccentricity as described above, in the case where a tomographic image is generated based on an acquired interference signal, distortion may be caused in the tomographic image due to a change in optical path length of the measurement light and a change in incident angle of the measurement light with respect to a fundus of the eye to be inspected being the object to be inspected, which are caused by alignment eccentricity.

SUMMARY OF THE INVENTION

In view of the foregoing, the present invention provides an image generating apparatus, an image generating method, and a computer-readable medium, which are capable of reducing distortion of a tomographic image caused by alignment eccentricity between measurement light and an object to be inspected.

According to one embodiment of the present invention, there is provided an image generating apparatus including: an acquisition unit configured to acquire tomographic data on an object to be inspected, the tomographic data being obtained by performing optical coherence tomography imaging of the object to be inspected through use of measurement light; an eccentric amount acquisition unit configured to acquire an eccentric amount of an optical axis of the measurement light with respect to the object to be inspected; and a generation unit configured to generate a tomographic image through use of the acquired tomographic data, wherein the generation unit includes: a calculation unit configured to calculate, through use of the eccentric amount, an incident angle variation of the measurement light entering the object to be inspected, and an optical path length variation of the measurement light entering the object to be inspected; and a correction unit configured to correct the tomographic data through use of the incident angle variation and the optical path length variation.

According to another embodiment of the present invention, there is provided an image generating method including: acquiring tomographic data on an object to be inspected, the tomographic data being obtained by performing optical coherence tomography imaging of the object to be inspected through use of measurement light; acquiring an eccentric amount of an optical axis of the measurement light with respect to the object to be inspected; and generating a tomographic image through use of the acquired tomographic data, wherein the generating a tomographic image includes: calculating, through use of the eccentric amount, an incident angle variation of the measurement light entering the object to be inspected, and an optical path length variation of the measurement light; and correcting the tomographic data through use of the incident angle variation and the optical path length variation.

Further features of the present invention will become apparent from the following description of exemplary embodiments with reference to the attached drawings.

DESCRIPTION OF THE EMBODIMENTS

Figure 1:
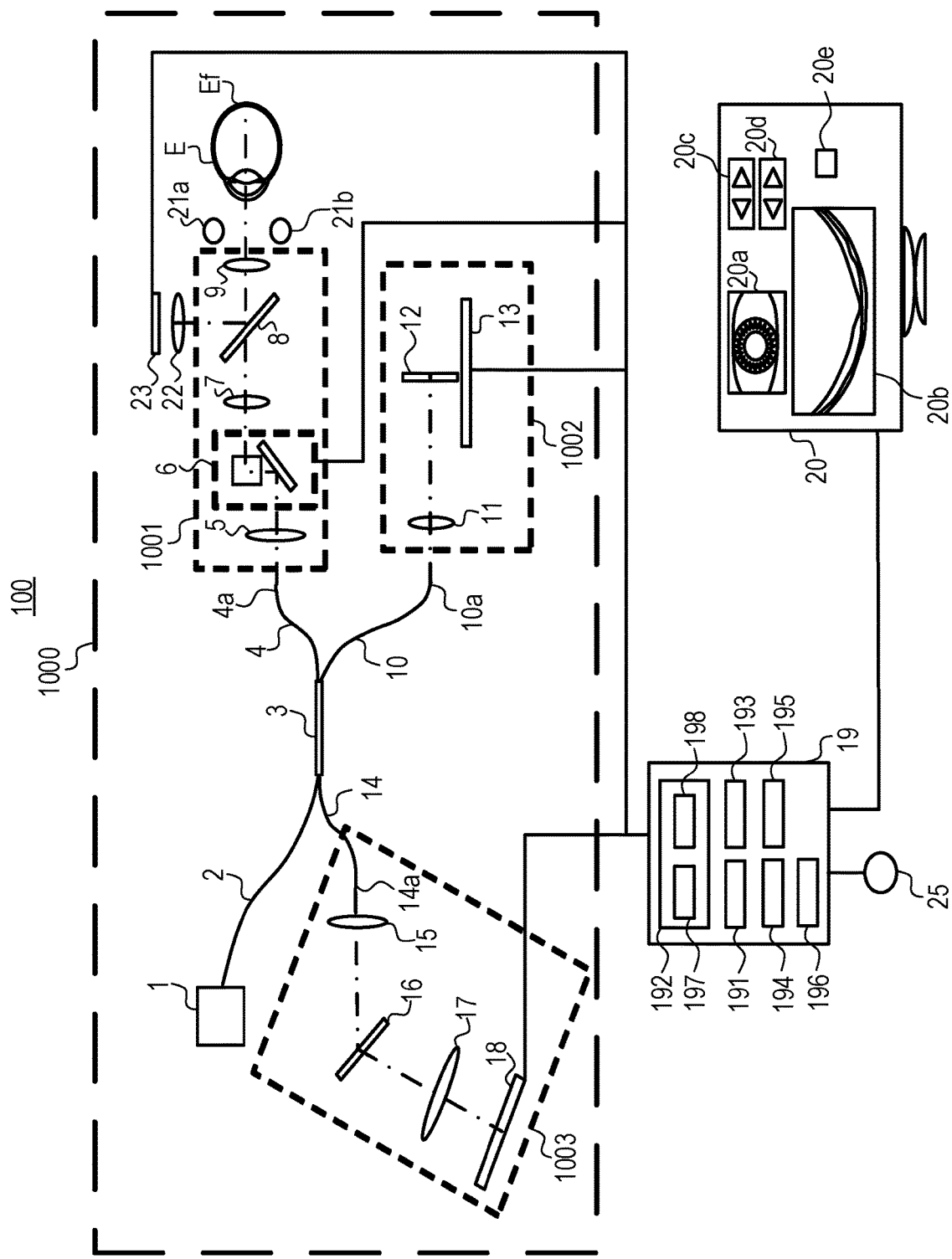
FIG. 1 is a diagram for illustrating a schematic configuration of an OCT apparatus in a first embodiment of the present invention.

Preferred embodiments of the present invention will now be described in detail in accordance with the accompanying drawings.

Dimensions, materials, shapes, relative positions of components, and the like described in the following embodiment are suitably selected and can be modified in accordance with a configuration of an apparatus to which the present invention is applied or various conditions. Further, in the drawings, like reference symbols are used in order to denote elements that are the same or similar in terms of function.

First Embodiment

With reference to FIG. 1 to FIG. 12, an OCT apparatus 100 is now described, which includes an image generating apparatus according to a first embodiment of the present invention, in particular, a tomographic image generating apparatus, and which uses an optical coherence tomography imaging method used for observing a fundus or the like.

(Apparatus Configuration)

A configuration of the OCT apparatus 100 is described with reference to FIG. 1. FIG. 1 is a diagram for illustrating a schematic configuration of the OCT apparatus 100 in the first embodiment.

The OCT apparatus 100 includes an imaging apparatus 1000, a controller 19, a display 20, and a pointing device 25. The imaging apparatus 1000 includes a light source 1, a light splitter 3, a sample arm 1001, a reference arm 1002, and a spectroscope 1003.

The light source 1 is a light source configured to generate light (low coherence light). In the first embodiment, a super luminescent diode (SLD) light source configured to emit light having a center wavelength of 850 nm and a band of 50 nm is used as the light source 1.

Alternatively, an amplified spontaneous emission (ASE) light source may be employed as the light source 1. In addition, an ultrashort pulse laser light source, for example, a titanium sapphire laser may be employed as the light source 1. In this way, any light source that can generate low coherence light may be employed as the light source 1. Further, a wavelength of light generated from the light source 1 is not particularly limited, and is selected in the range of from 400 nm to 2 μm depending on the object to be inspected. In the OCT, as the band width of the wavelength becomes wider, the longitudinal resolution of a tomographic image becomes higher. In general, when the center wavelength is 850 nm, a band width of 50 nm makes a longitudinal resolution of 6 μm while a band width of 100 nm makes a longitudinal resolution of 3 μm.

Light guides 2, 4, 10, and 14 are each formed of an optical fiber or the like. A light flux emitted by the light source 1 is guided to the light splitter 3 by the light guide 2. The light splitter 3 can be formed of a fiber coupler or the like. A split ratio can be suitably selected in accordance with the object to be inspected.

On an optical path split by the light splitter 3 to the light guide 4 side, there is arranged the sample arm 1001 including a collimator lens 5, a light scanner 6, a focus lens 7, a wavelength branching mirror 8, and an objective lens 9. As the light scanner 6, an X-scan mirror and a Y-scan mirror, such as Galvano mirrors and resonant mirrors, which are arranged adjacent to each other in an optical axis direction (tandem arrangement) and configured to scan measurement light in X and Y directions orthogonal to each other, are employed. The wavelength branching mirror 8 transmits the light (wavelength: λ=800 nm to 900 nm) emitted by the light source 1, and reflects light (λ=940 nm) of an anterior segment illumination light source. The light guided to the light guide 4 passes through the sample arm 1001 as measurement light to reach a fundus Ef of an eye E to be inspected. The focus lens 7 is arranged so as to be movable in the optical axis direction by a motor or the like (not shown) controlled by the controller 19.

On an optical path split by the light splitter 3 to the light guide 10 side, there is arranged the reference arm 1002 including a collimator lens 11 and a reference mirror 12. The reference mirror 12 is arranged on a linear stage 13, and an optical path length of the reference arm 1002 can be adjusted by moving the linear stage 13 in the optical axis direction to move the position of the reference mirror 12. The reference mirror 12 and the linear stage 13 serve as an adjuster configured to adjust the optical path length of reference light.

On an optical path split by the light splitter 3 to the light guide 14 side, the spectroscope 1003 is arranged. The spectroscope 1003 includes a lens 15, a spectroscopic member 16 formed of a grating being a diffraction grating, a prism, or the like, an imaging lens 17, and an imaging device 18 including photoelectric conversion elements such as a CMOS or a CCD. Return light of the measurement light from the eye E to be inspected and the reference light are combined in the light splitter 3 to generate interference light. The interference light is guided to the spectroscope 1003 by the light guide 14 connected to the light splitter 3. The imaging device 18 of the spectroscope 1003 detects the interference light to image the fundus Ef of the eye E to be inspected. The interference signal output from the imaging device 18 is transmitted to the controller 19, and the controller 19 generates a tomographic image based on the interference signal.

Anterior segment illumination light sources 21a and 21b are arranged on the periphery of the objective lens 9. The return light of an anterior segment of the eye E to be inspected illuminated by the anterior segment illumination light sources 21a and 21b passes through the objective lens 9 and is reflected by the wavelength branching mirror 8 to form an image on an imaging surface of a two-dimensional imaging device 23 by a lens 22. An image signal output from the imaging device 23 is transmitted to the controller 19, and the controller 19 generates an anterior segment image based on the output from the imaging device 23.

The controller (image generating apparatus) 19 includes an acquisition unit 191, an image generation unit 192, an eccentric amount acquisition unit 193, a drive control unit 194, a storage 195, and a display control unit 196. Further, the controller 19 is connected to the light scanner 6, the linear stage 13, and the imaging devices 18 and 23.

The acquisition unit 191 is configured to acquire information on a scanning angle from the light scanner 6, the interference signal from the imaging device 18, the image signal from the imaging device 23, and the like. The image generation unit (generation unit) 192 is configured to generate a tomographic image and an anterior segment image based on various signals acquired in the acquisition unit 191. The eccentric amount acquisition unit 193 is configured to acquire an eccentric amount between an optical axis of the imaging apparatus 1000 and an optical axis of the eye E to be inspected at a time of tomography imaging by a method described later.

The drive control unit (positioning unit) 194 is configured to control the light scanner 6, the focus lens 7, the linear stage 13, a stage (not shown) configured to drive the sample arm 1001, and the like. The storage 195 is configured to store information on a subject to be examined input to the controller 19, various images generated in the controller 19, a program for causing the controller 19 to function, and the like. The display control unit 196 is configured to control display of the display 20 connected to the controller 19.

The image generation unit 192 includes a calculation unit 197 and a correction unit 198. The calculation unit 197 is configured to calculate an incident angle variation of the measurement light with respect to the fundus Ef of the eye E to be inspected and an optical path length variation of the measurement light, based on the eccentric amount acquired in the eccentric amount acquisition unit 193. The correction unit 198 is configured to correct the tomographic image based on the incident angle variation and the optical path length variation. Calculation methods for an incident angle variation and an optical path length variation, and a correction method for a tomographic image are described later in detail.

Each component of the controller 19 can be formed of a module implemented by a central processing unit (CPU) or a micro processing unit (MPU) of the controller 19. Further, each component of the controller 19 may be formed of a circuit for implementing a specific function, for example, an application specific integrated circuit (ASIC). The storage 195 can be formed through use of any storage device or storage medium such as a memory or an optical disc. The storage 195 may be connected to the controller 19 as an external storage device or storage medium.

Further, the controller 19 is connected to the display 20 and the pointing device 25, for example, a mouse. The display 20 is configured to display various images output from the controller 19, information on the subject to be examined, and the like. The pointing device 25 serves as an input device with which a user performs input to the controller 19.

Next, an imaging method for taking a tomographic image of a retina in the fundus Ef of the eye E to be inspected through use of the OCT apparatus 100 is described.

After the eye E to be inspected is set in front of the imaging apparatus 1000, in the OCT apparatus 100, the anterior segment of the eye E to be inspected is illuminated by light emitted from the anterior segment illumination light sources 21a and 21b. Return light from the illuminated anterior segment passes through the objective lens 9 and is reflected by the wavelength branching mirror 8 to form an image on the imaging surface of the imaging device 23 by the lens 22. The acquisition unit 191 of the controller 19 acquires an image signal from the imaging device 23, and the image generation unit 192 converts the acquired image signal into digital data in real time to generate an anterior segment image.

The controller 19 can also determine eccentricity of the eye E to be inspected and a focus state thereof based on the anterior segment image, particularly a pattern of an iris of the eye E to be inspected. The center of the imaging device 23 is adjusted to be matched with the optical axis of an optical system of the sample arm 1001 in the imaging apparatus 1000, and hence an eccentricity amount between the pupil center of the anterior segment image taken by the imaging device 23 and the center of the anterior segment image corresponds to an eccentricity amount between the eye E to be inspected and the optical system of the sample arm 1001. The anterior segment image is displayed on a display region 20a of the display 20, and an operator can confirm optical axis eccentricity from the displayed anterior segment image.

The optical system of the sample arm 1001 in the imaging apparatus 1000 is arranged on a stage (not shown) so that the position thereof can be adjusted in upper, lower, left, and right directions with respect to the eye E to be inspected, and further in an optical axis direction. When a tomographic image is normally taken, the drive control unit 194 adjusts the positions in upper, lower, left, and right directions of the optical system of the sample arm 1001 so that the optical axis of the measurement light is matched with the pupil center, and adjusts the position in the optical axis direction so that the contrast of the pattern of the iris becomes the maximum. The positioning between the imaging apparatus 1000 and the eye E to be inspected by the drive control unit 194 is hereinafter referred to as "auto-alignment". With this, the distance (working distance) between the pupil of the eye E to be inspected, which is flush with the iris, and the objective lens 9 of the optical system of the sample arm 1001 is kept constant.

When the eccentric amount becomes a predetermined value or less due to auto-alignment, the OCT apparatus 100 turns on the light source 1 to start taking a tomographic image for alignment. The light from the light source 1 is guided to the light splitter 3 through the light guide 2. The light splitter 3 splits the light from the light guide 2 so that the ratio of optical amounts guided to the light guides 4 and 10 reaches, for example, 1:9. The measurement light guided to the light guide 4 side reaches a fiber end 4a. The measurement light emitted from the fiber end 4a serving as a point light source is converted into collimated light by the collimator lens 5 and scanned by the X-scan mirror of the light scanner 6. The measurement light converted into collimated light is transmitted through the focus lens 7 and the wavelength branching mirror 8, to thereby irradiate the fundus Ef from the pupil of the eye E to be inspected by the objective lens 9 and scan the fundus Ef.

Further, the reference light guided to the light guide 10 through the light splitter 3 is output from a fiber end 10a. Then, the reference light is converted into collimated light by the collimator lens 11 and directed to the reference mirror 12. The reference mirror 12 is arranged on the linear stage 13 perpendicularly to an optical axis of the collimated reference light so as to be movable in the optical axis direction. With this, by moving the reference mirror 12 with the linear stage 13, the optical path length of the optical path of the reference light can be matched with the optical path length of the optical path of the measurement light also with respect to the eye E to be inspected having a different eye axial length. The operator is capable of adjusting the position of the reference mirror 12 by operating the pointing device 25 to designate a display region 20*d* on the display 20 with a cursor. The position of the reference mirror 12 may be automatically adjusted by the controller 19 based on the acquired tomographic image and the like.

The reference light reflected by the reference mirror 12 is converged onto the fiber end 10*a* of the light guide 10 by the collimator lens 11 and guided to the light splitter 3 by the light guide 10. The return light of the measurement light from the fundus Ef and the reference light are combined in the light splitter 3 and guided to the light guide 14 as interference light. The interference light guided to the light guide 14 enters the spectroscope 1003 and is output from a fiber end 14*a* of the light guide 14. Then, the interference light is spectrally diffracted by the spectroscopic member 16 to form an image on a light-receiving region of the imaging device 18 in which photoelectric conversion elements are linearly arrayed as described above. An interference signal output from the imaging device 18 is input to the controller 19. The controller 19 subjects the interference signal to Fourier transform or the like to generate a tomographic image.

The display 20 displays the generated tomographic image on a display region 20*b*. The operator observes the tomographic image and performs focus adjustment by operating buttons in a display region 20*c* with the cursor through use of the pointing device 25 so that the tomographic image becomes brightest. The drive control unit 194 of the controller 19 drives a motor (not shown) or the like in accordance with the operation of the buttons to move the focus lens 7 along the optical axis, to thereby change the focus of the measurement light. Further, the operator performs position alignment (coherence gate adjustment) of the reference mirror 12 similarly by operating buttons in the display region 20*d* so that the entire tomographic image of a part of interest is contained within a desired area of the display region 20*b*. The drive control unit 194 drives a stepping motor (not shown) for moving the linear stage 13 in accordance with the operation of the buttons to move the linear stage 13 along the optical axis, to thereby change the position of the reference mirror 12. When a direction on the display region 20*d* is designated, the controller 19 moves the position of the linear stage 13 in the designated direction. Simultaneously, the controller 19 changes the control position information of the linear stage 13 stored in the storage 195 in accordance with the movement amount.

The linear stage 13 is driven and controlled by the stepping motor (not shown), and the position of the linear stage 13 corresponds to the number of steps designated to the stepping motor. For example, when a stroke of 60 mm is driven by 60,000 steps, the movement amount per step is 1 μm. In this case, the number of steps of from 0 to 60,000 corresponds to the position of from 0 mm to 60 mm of the linear stage 13. Further, the distance from a reference position of the linear stage 13 to the collimator lens 11 is set with high accuracy in terms of design, and the relationship between the reference position and the stage position is apparent in terms of design. Therefore, the optical path length of the reference light can be calculated based on the number of steps. Accordingly, the controller 19 can detect the optical path length of the reference light based on the number of steps of the stepping motor (not shown).

The optical path length of the reference light changes along with the change in position of the reference mirror 12. When the optical path length of the measurement light and the optical path length of the reference light become substantially equal to each other, the return light of the measurement light and the reference light interfere with each other to form interference light. Therefore, when the optical path length of the reference light is changed, the optical path length of the measurement light that interferes with the reference light changes, and the imaging position of the eye E to be inspected in the optical axis direction changes. Thus, when the position of the reference mirror 12 is changed, the display position of the tomographic image in the display region 20*b* can be changed. The storage 195 constantly stores the position of the reference mirror 12 at a time of tomography imaging. When an imaging button 20*e* is operated after the above-mentioned preparation for imaging, the OCT apparatus 100 takes a still image of the tomographic image (tomography imaging). The storage 195 stores the taken tomographic image. In the foregoing, the operator designates adjustment of a focus and a coherence gate, but the controller 19 may automatically adjust a focus and a coherence gate based on the taken tomographic image and the like.

Next, tomographic image generation by the controller 19 is described. The combined light of the return light of the measurement light from the fundus Ef of the eye E to be inspected and the reference light reflected by the reference mirror 12 is guided as the interference light to the light guide 14. Because of a difference between the optical path length from the light splitter 3 to the fundus Ef and the optical path length from the light splitter 3 to the reference mirror 12, there is a phase difference between the return light of the measurement light and the reference light when being combined by the light splitter 3. The phase difference varies depending on the wavelength, and hence interference fringes are generated in a spectral intensity distribution appearing in a light-receiving region of the imaging device 18. Further, the retina includes a plurality of layers, and return light from each layer boundary has a different optical path length. Therefore, the interference fringes include interference fringes having different frequencies. The controller 19 can determine the position of a reflective object and the brightness corresponding to the reflection and scattering from the position based on the frequencies and the intensities of the interference fringes included in the intensity distribution.

Herein, a scan system of acquiring a tomographic image in a depth direction (Z direction) at one certain point of the fundus Ef of the eye E to be inspected is referred to as "A-scan", and a tomographic image to be obtained by the A-scan is referred to as "A-scan image". Further, when the A-scan is repeatedly performed while the fundus Ef is scanned in a predetermined transverse direction with the measurement light by the light scanner 6, a plurality of A-scan images can be acquired. For example, when the measurement light is scanned in the X direction by the light scanner 6, a tomographic image on an XZ plane is obtained. When the measurement light is scanned in the Y direction, a tomographic image on a YZ plane is obtained. A system of scanning the fundus Ef of the eye E to be inspected in a predetermined transverse direction is referred to as "B-scan", and a tomographic image to be obtained by the B-scan is referred to as "B-scan image".

In a B-scan mode of scanning one line on the fundus Ef, the acquisition unit 191 acquires the interference signal from the imaging device 18 while the drive control unit 194 drives one of the X-scan mirror and the Y-scan mirror of the light scanner 6, for example, only the X-scan mirror. In this case, the acquisition unit 191 also acquires data indicating an angle of the scan mirror output from the light scanner 6. The controller 19 converts the acquired interference signal into digital data together with the angle of the scan mirror. The controller 19 further converts the data on the angle of the scan mirror into an incident angle θi of the measurement light with respect to the eye E to be inspected and stores the incident angle θi in the storage 195. The angle of the scan mirror and the incident angle θi of the measurement light correspond to each other and can be determined based on a design value of the optical system. The incident angle θi corresponds to an angle forced by the measurement light that enters the eye E to be inspected and an ocular axis of the eye E to be inspected.

Figure 2:
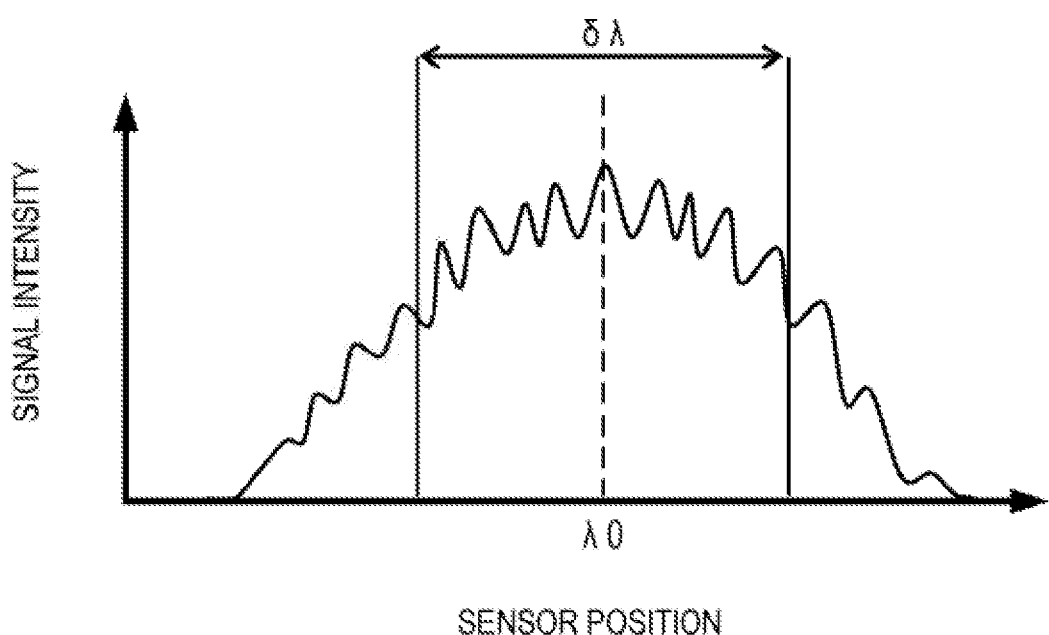
FIG. 2 is a graph for showing an example of an intensity distribution of interference light.

FIG. 2 is a graph for showing an example of an intensity distribution of interference light on the imaging device 18 at an angle of the scan mirror corresponding to the incident angle θi. The horizontal axis represents a sensor position on the imaging device 18 and corresponds to a wavelength. The vertical axis represents signal intensity. In this case, a waveform caused by interference fringes overlap a center wavelength λ0 and a half width δλ of an intensity distribution.

Figure 3:
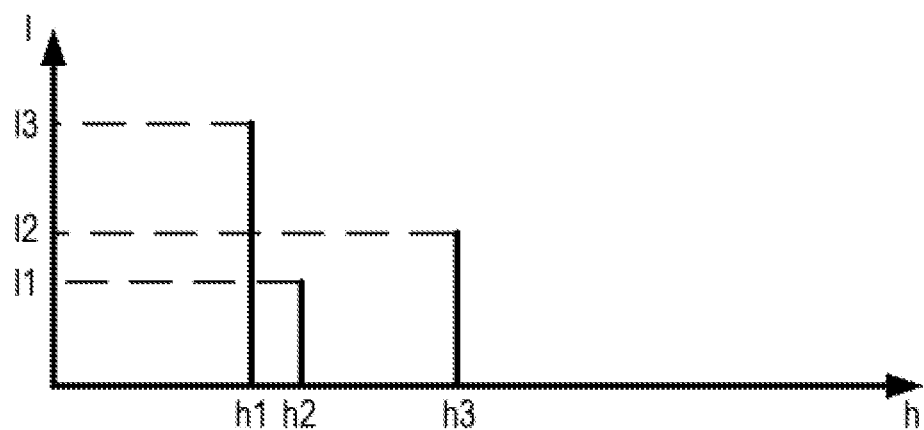
FIG. 3 is a graph for showing an example of an interference signal after frequency conversion.

The controller 19 reads intensity information of a waveform of an interference signal corresponding to a waveform of the interference light. The controller 19 converts the read intensity information into digital data with an A/C converter and stores the digital data in the storage 195. The image generation unit 192 subjects the converted digital data to wave number conversion and frequency conversion through fast Fourier transform or the like to obtain an intensity distribution for each frequency. FIG. 3 is a graph for showing an example of the intensity distribution. In FIG. 3, the horizontal axis represents a frequency, which corresponds to a distance h from a coherence gate position in the tomographic image generated based on the interference signal, and the vertical axis represents an intensity I. Further, FIG. 4 is a diagram for illustrating an example of a tomographic image generated through use of the interference signal.

Figure 4:
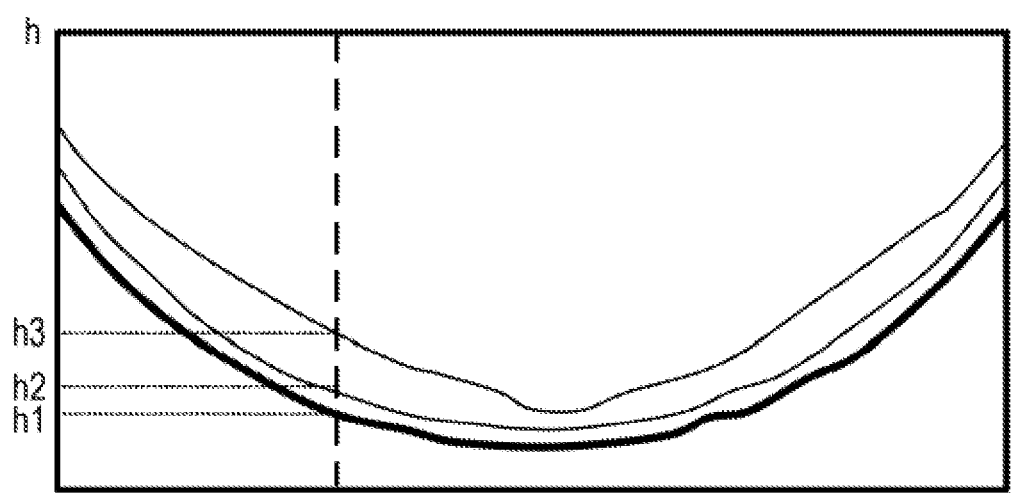
FIG. 4 is a diagram for illustrating an example of a tomographic image based on an interference signal.

The intensity distribution shown in FIG. 3 indicates that interference intensities at distances (from the coherence gate) h1, h2, and h3 are I3, I1, and I2, respectively, as illustrated in FIG. 4. The coherence gate position corresponds to an optical path length with which the measurement light and the reference light cause interference as described above, and corresponds to the position of the reference mirror 12. In the first embodiment, the coherence gate position corresponds to a lower end of the tomographic image.

The controller 19 measures intensity of the interference signal while changing the incident angle θi corresponding to the angle of the scan mirror from an angle θs at a time of start of scanning to an angle θe at a time of ending of scanning. The image generation unit 192 can generate a B-scan image (image based on an optical distance) of the fundus Ef as illustrated in FIG. 4 by arranging the intensity I (θi, hj) of the interference signal with θ being the horizontal axis and h being the vertical axis. Further, the controller 19 can generate a three-dimensional tomographic signal and tomographic image by repeating the B-scan in the Z and X directions in the Y direction with the measurement light. The controller 19 may repeatedly perform the B-scan in the Z and Y directions in the X direction with the measurement light. Further, the tomographic image may be generated by any known method other than the above-mentioned method.

(Alignment Eccentricity)

Figure 5A:
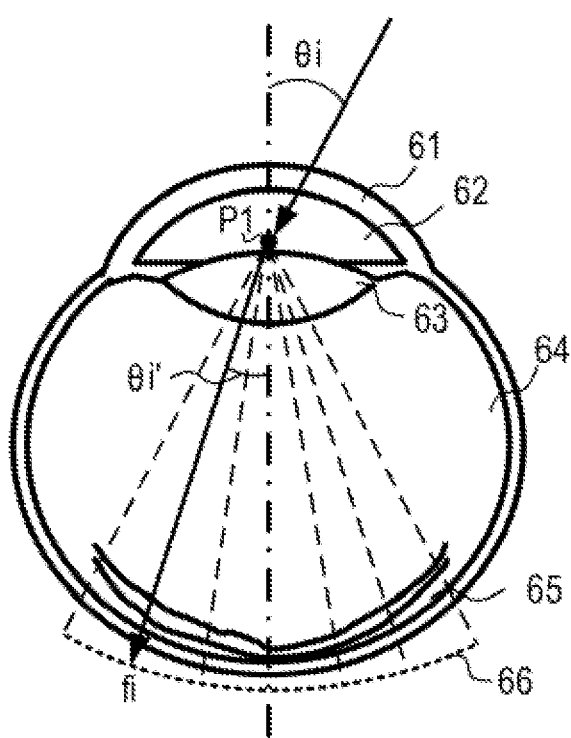
FIG. 5A is a view for illustrating measurement light that enters an eye to be inspected.
Figure 5B:
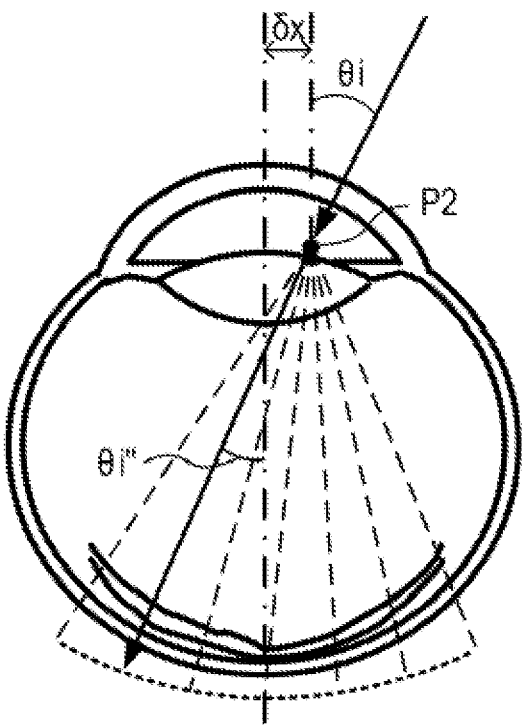
FIG. 5B is a view for illustrating the measurement light that enters the eye to be inspected.

FIG. 5A and FIG. 5B are each a view for illustrating an example of a light beam of the measurement light reaching the fundus Ef when the fundus Ef is subjected to the B-scan. FIG. 5A is a view for illustrating an example of ideal alignment with the eye E to be inspected. In FIG. 5A, an optical axis of the eye E to be inspected and an optical axis of the imaging apparatus 1000 (optical axis of the measurement light) that are matched with each other is represented by the alternate long and short dash line. The light beam that enters the eye E to be inspected at the incident angle θi through a cornea 61 passes through a center portion of a pupil 62, a crystalline lens 63, and a vitreous body 64 in the eye E to be inspected, and is directed to a fundus 65 at the incident angle θi to be reflected to scatter in each layer of the retina.

The X-scan mirror is designed so as to be conjugated with the pupil 62 when the distance between the eye E to be inspected and the optical system of the sample arm 1001 is suitably kept by an auto-alignment function. Therefore, even when a scan angle of the X-scan mirror changes, the light beam constantly passes through a point P1 at the center portion of the pupil 62. The point P1 is referred to as "pivot point". The pivot point P1 corresponds to a position through which the measurement light constantly passes even when the measurement light is caused to enter the inside of the eye E to be inspected and scanned on the retina. Therefore, the pivot point P1 corresponds to an incident point of the measurement light with respect to the eye E to be inspected when the measurement light is scanned on the retina inside the eye E to be inspected.

Further, in FIG. 5A, there is illustrated a position at which the optical path length of the measurement light and the optical path length of the reference light have the same distance, that is, a coherence gate position 66 equivalent to the position of the reference mirror 12. The distances h1, h2, and h3 determined based on the interference signal correspond to the distances between the coherence gate position 66 and each retinal layer. When the eye E to be inspected having a different ocular axis length is imaged, suitable measurement can be performed by adjusting the linear stage 13 to align the position of the reference mirror 12 with the ocular axis length.

Meanwhile, in OCT imaging, there may be a case in which alignment with the eye E to be inspected is not perfect, and the measurement light is caused to enter from a peripheral portion of the pupil to image the eye E to be inspected under a state in which auto-alignment is canceled. This case corresponds to, for example, a case in which there is opacity in intermediate optic media such as a crystalline lens due to cataract, and an optical path in the center portion of the pupil is interrupted, and a case in which an incident angle to the retina is changed to avoid artifact caused by the shadow of a blood vessel. Further, there is a case in which alignment eccentricity is intentionally caused also when an incident angle of the measurement light entering the retina is set to be close to a perpendicular direction to increase an optical amount of the return light by reflection. In contrast, as the case in which alignment eccentricity is unintentionally caused, there is given a case in which fixation of the eye E to be inspected is unstable, and alignment is not fixed.

In the above-mentioned cases, a change in optical characteristics with respect to the eye E to be inspected described below may have an effect on the shape of a tomographic image to be generated to cause distortion in the tomographic image.

FIG. 5B is a view for illustrating a case in which parallel eccentricity occurs in alignment with the eye E to be inspected in the imaging apparatus 1000. In FIG. 5B, an optical axis of the eye E to be inspected and an optical axis of the imaging apparatus 1000 are represented by the alternate long and short dash line. In the same manner as in FIG. 5A, the light beam of the measurement light that enters the eye E to be inspected at the incident angle θi through the cornea 61 passes through peripheral portions of the pupil 62 and the crystalline lens 63, and passes through the vitreous body 64. Then, the measurement light is directed to the fundus 65. When an alignment eccentric amount is represented by δx, a pivot point represented by a point P2 is also displaced from the optical axis of the eye E to be inspected by δx. Further, the focus is on the retina, and hence a converged point of the light flux on the retina remains unchanged. Therefore, even when parallel eccentricity occurs in the light beam of the measurement light in each scanning, a reaching point of the light flux on the retina remains unchanged. Meanwhile, regarding the incident angle to the fundus 65, the measurement light is directed at an angle θi″ different from that in the case of ideal alignment.

(Change in Incident Angle Caused by Alignment Eccentricity)

Figure 6:
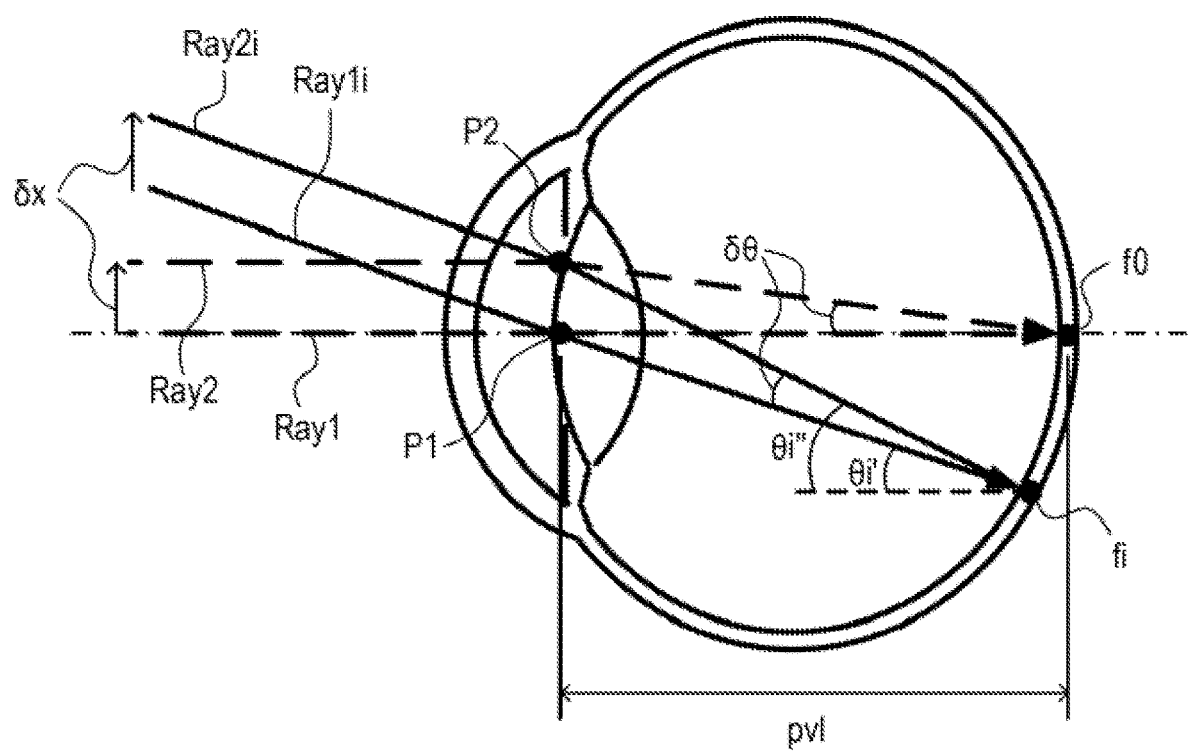
FIG. 6 is a view for illustrating an example of a change in fundus incident angle of the measurement light.

Now, a change in incident angle of the measurement light with respect to the retina caused by alignment eccentricity is described with reference to FIG. 6. FIG. 6 is a view for illustrating a state in which the measurement light enters the eye E to be inspected while being scanned. In FIG. 6, there are illustrated a center scanning ray Ray1, a peripheral scanning ray Ray1$i$, and the pivot point P1 in the case of ideal alignment. Similarly, there are also illustrated a center scanning ray Ray2, a peripheral scanning ray Ray2$i$, and the pivot point P2 in the case of occurrence of alignment eccentricity. Herein, the center scanning ray refers to a light beam of the measurement light for scanning a center portion of the fundus Ef, and the peripheral scanning ray refers to a light beam of the measurement light for scanning a peripheral portion of the fundus Ef. In FIG. 6, the center scanning ray is represented by the broken line, the peripheral scanning ray is represented by the solid line, and the optical axis of the eye E to be inspected is represented by the alternate long and short dash line.

When alignment eccentricity occurs, the light beam before entering the eye E to be inspected is subjected to parallel eccentricity with respect to the eye E to be inspected by the same amount and in the same direction irrespective of whether the light beam is the center scanning ray (Ray1, Ray2) or the peripheral scanning ray (Ray1$i$, Ray2$i$). An incident angle variation δθ of the measurement light entering the retina caused by alignment eccentricity is regarded as an angle of the center scanning ray Ray2 after entering the eye E to be inspected with respect to the center scanning ray Ray1. When an alignment eccentric amount is represented by δx, from a triangle P1f0P2 formed by a retina reaching point f0 and the pivot points P1 and P2, the following expression is obtained.

$$\angle P1f0P2 = \delta\theta \approx \tan\delta\theta = \delta x/pvl \quad \text{(Expression 1)}$$

The symbol "pvl" represents a distance from the pivot point to the retina and can be determined based on the position of the retina in the tomographic image, the position of the reference mirror 12, and the distance (working distance) between the imaging apparatus 1000 and the eye E to be inspected. Further, the eccentric amount acquisition unit 193 of the controller 19 can calculate the alignment eccentric amount δx by analyzing an anterior segment image based on an image signal from the imaging device 23. Thus, the incident angle variation δθ can be uniquely determined.

Meanwhile, an angle of the peripheral scanning ray Ray2$i$ after entering the eye E to be inspected with respect to the peripheral scanning ray Ray1$i$ is considered. When a cross section of an eye ball is regarded as a circle, from a triangle P1fiP2 formed by a retina reaching point fi and the pivot points P1 and P2, $\angle P1fiP2 = \angle P1f0P2 = \delta\theta$ is obtained based on a relationship of a geometric circumferential angle. Therefore, the incident angle variation of the measurement light entering the retina caused by alignment eccentricity is constantly δθ irrespective of the scanning direction. Further, a relationship between an incident angle θi′ of the measurement light entering the retina in the case of ideal alignment and the angle θi″ thereof in the case of occurrence of alignment eccentricity is represented by θi″=θi′+δθ.

(Change in Optical Path Length Caused by Alignment Eccentricity)

Figure 7A:
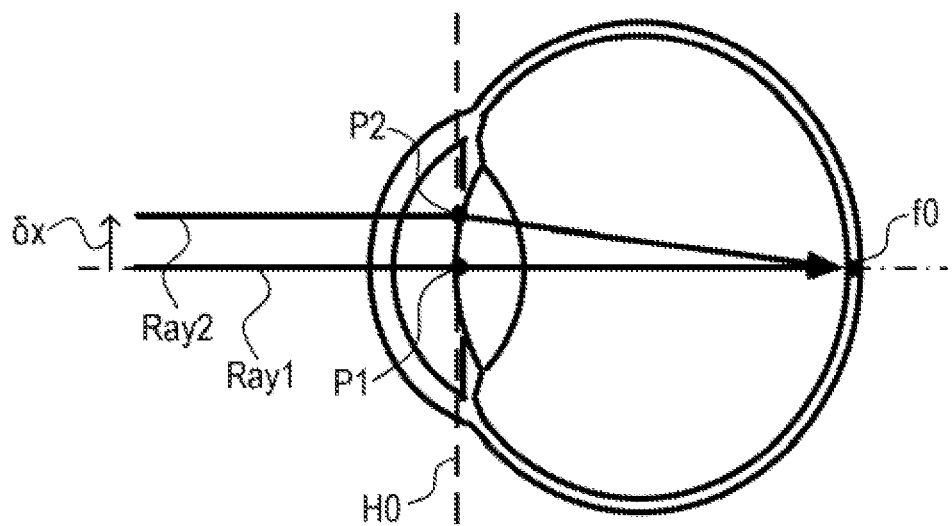
FIG. 7A is a view for illustrating an example of a change in optical path length of the measurement light.
Figure 7B:
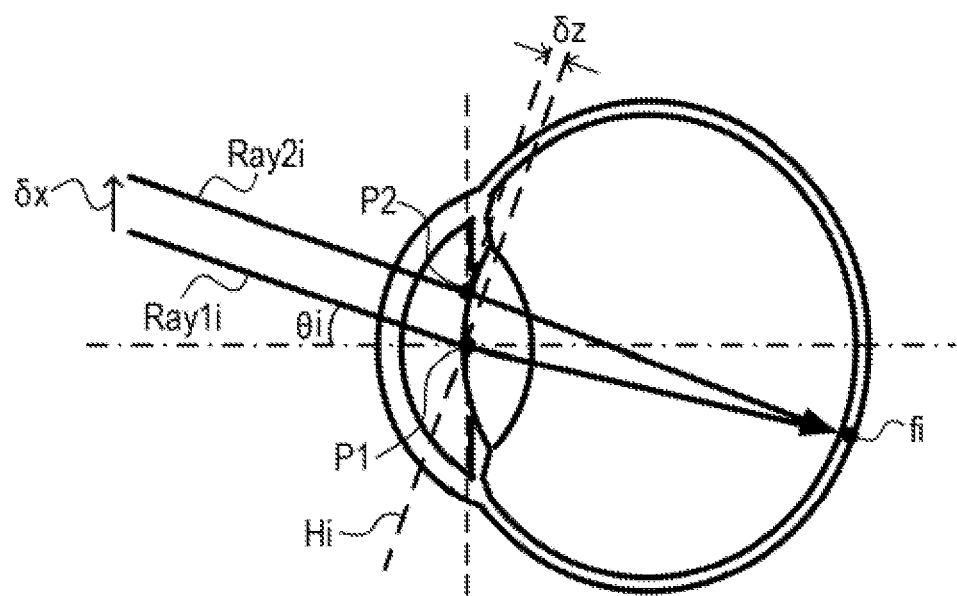
FIG. 7B is a view for illustrating an example of a change in optical path length of the measurement light.

When alignment eccentricity occurs, the optical path length of the measurement light also changes. FIG. 7A and FIG. 7B are each a view for illustrating a change in optical path length of the measurement light when alignment eccentricity occurs. FIG. 7A is a view for illustrating a difference in alignment state in the center scanning rays Ray1 and Ray2. The center scanning ray Ray1 is a light beam of the measurement light in an ideal alignment state, and the center scanning ray Ray2 is a light beam of the measurement light in an alignment eccentricity occurrence state. Further, in FIG. 7A, there is illustrated a front-side main plane H0 in the center scanning ray, and the front-side main plane H0 is a plane perpendicular to the optical axis of the eye E to be inspected. In this case, even when the optical path of the measurement light is changed from the optical path of the center scanning ray Ray1 to the optical path of the center scanning ray Ray2 due to eccentricity having a direction indicated by the vector of FIG. 7A and the alignment eccentric amount δx, the optical path length to the front-side main plane H0 does not change. In any case, the measurement light enters the front-side main plane H0 and then is output from a back-side main plane (not shown) to reach the same retina reaching point f0 with the same optical path length.

Meanwhile, FIG. 7B is a view for illustrating a difference in alignment state in the peripheral scanning rays Ray1$i$ and Ray2$i$. The peripheral scanning ray Ray1$i$ is a light beam of the measurement light in an ideal alignment state, and the peripheral scanning ray Ray2$i$ is a light beam of the measurement light in an alignment eccentricity occurrence state. Further, in FIG. 7B, there is illustrated an incident angle θi of the measurement light with respect to the eye E to be inspected.

Consideration is now given of a case in which the incident angle θi of the measurement light (information on the scanning angle of the measurement light) used for, for example, wide field angle imaging of the eye E to be inspected is sufficiently large. In this case, an optical model that also takes an off-axis ray into consideration is adopted instead of optical paraxial theory. That is, a front-side main plane Hi corresponding to the measurement light at the incident angle θi is a plane perpendicular to the peripheral scanning ray Ray1$i$ instead of the optical axis of the eye E to be inspected. Consideration is given of a case in which the optical path of the measurement light is changed from the optical path of the peripheral scanning ray Ray1$i$ to the optical path of the peripheral scanning ray Ray2$i$ due to eccentricity having a direction indicated by the vector of FIG. 7B and the alignment eccentric amount δx. In this case, the direction of the eccentricity is different from that of the front-side main plane Hi, and hence a difference of an optical path length variation δz is caused between the optical path lengths of the peripheral scanning rays Ray1$i$ and Ray2$i$ up to the front-side main plane Hi. In this case, based on a geometric relationship, the optical path length variation δz can be represented by the following expression.

$$\delta z = \delta x \times \sin \theta i \quad \text{(Expression 2)}$$

Thus, when the peripheral portion of the fundus Ef is scanned under a state in which alignment eccentricity occurs, a tomographic image reflecting the optical path length variation δz in accordance with the incident angle θi of the measurement light is taken irrespective of the shape of the fundus Ef. Therefore, when alignment eccentricity occurs, changes are caused in the incident angle and the optical path length of the measurement light with respect to the fundus Ef, which are assumed in scanning of the measurement light in the light scanner 6, and thus a tomographic image generated through use of the measurement light is distorted. The alignment eccentric amount δx is obtained from the anterior segment image, and the incident angle θi is obtained from information on the angle of the scan mirror. Therefore, the optical path length variation δz can be uniquely determined.

Figure 8A:
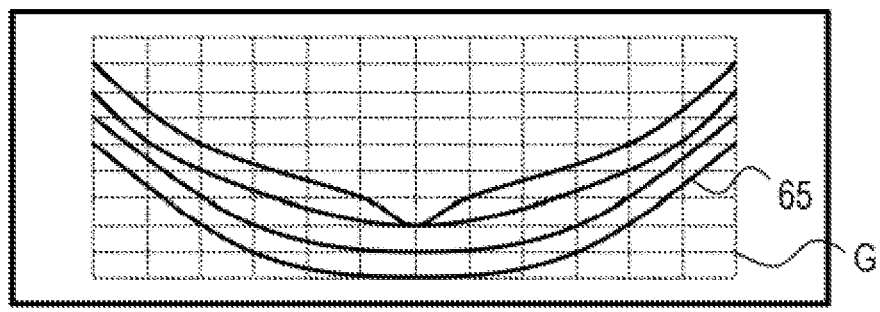
FIG. 8A is a view of a tomographic image, for illustrating influence of alignment eccentricity.
Figure 8B:
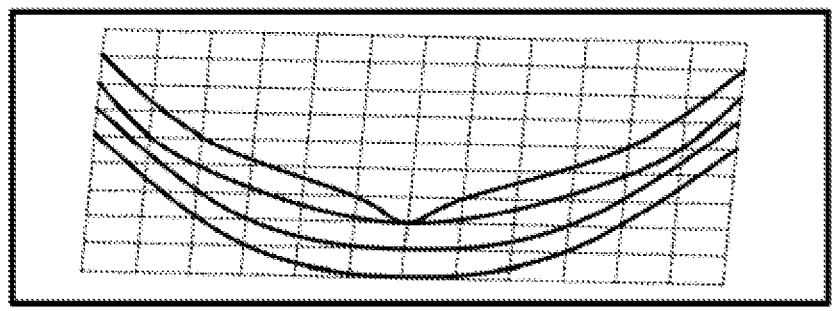
FIG. 8B is a view of a tomographic image, for illustrating influence of alignment eccentricity.

Next, with reference to FIG. 8A and FIG. 8B, distortion of a tomographic image exhibited when alignment eccentricity occurs is described. FIG. 8A and FIG. 8B are each a view for illustrating influence of a difference in alignment state on a tomographic image. FIG. 8A is a view for illustrating an example of a tomographic image obtained when the alignment state of the imaging apparatus 1000 is ideally matched with the optical axis of the eye E to be inspected. In each of FIG. 8A and FIG. 8B, the state of the fundus 65 and a lattice grid G for comparison are illustrated.

Meanwhile, FIG. 8B is a view for illustrating an example of a tomographic image obtained when alignment eccentricity occurs. In this case, the tomographic image becomes an image that appears to be rotated as a whole as compared to that of FIG. 8A due to the influence of changes in incident angle and optical path length of the measurement light with respect to the fundus 65 described above. In the generated tomographic image, the perpendicular direction of the image corresponds to the incident direction of the measurement light, and the perpendicular distance corresponds to the optical path length. Therefore, when alignment eccentricity occurs, the incident direction is uniformly inclined, and the optical path length linearly changes in accordance with the B-scan. Those relationships correspond to Expression 1 and Expression 2. Accordingly, distortion is caused in a generated tomographic image when alignment eccentricity occurs.

(Actual Shape Correction)

The shape of the fundus shown in the tomographic image of FIG. 8A is different from the shape of the fundus Ef in the actual eye ball. Specifically, a normal tomographic image is generated so that data corresponding to angles of the scan mirror is arranged in parallel. However, actually, the image data is to be expressed on a polar coordinates system having a scan center (pivot point) as its center as illustrated in FIG. 5A. Thus, when the shape of the fundus is analyzed in more detail, a tomographic image, which is normally generated, can be subjected to actual shape correction so that the shape of the fundus 65 in the tomographic image is approximated to the actual shape of the fundus Ef.

In the actual shape correction, a tomographic image generated based on data arranged on X-Y coordinates is corrected by rearranging data that is contained in the tomographic image on the polar coordinates system having the pivot point as its center. More specifically, a value obtained by dividing an optical distance from the pivot point P1 to the retinal layer by a refractive index of a refractive element in the eye E to be inspected, and an angle formed by the optical axis of the measurement light and a line segment connecting the retina reaching point fi (irradiation position) of the measurement light in the fundus Ef to the pivot point P1 are determined. Then, the tomographic image is corrected through use of the polar coordinates system having the pivot point P1 as an origin, with the determined value and angle being parameters.

The actual shape correction may be performed by any other known methods. For example, in Japanese Patent Application Laid-Open No. 2012-148003, there is disclosed a technology capable of obtaining a tomographic image of the eye E to be inspected having a shape close to an actual shape by determining data for generating the tomographic image through use of optical information (a refractive index of a refractive element, a relationship of a scanning angle with respect to an incident angle, and the like) of the eye E to be inspected and an optical path length. In Japanese Patent Application Laid-Open No. 2012-148003, it is described that the distance "pvl" from the pivot point to the retina surface, which corresponds to an ocular axis length of the eye E to be inspected, is determined based on the optical path length of the reference light. However, the ocular axis length may be determined by a separate apparatus.

Figure 9A:
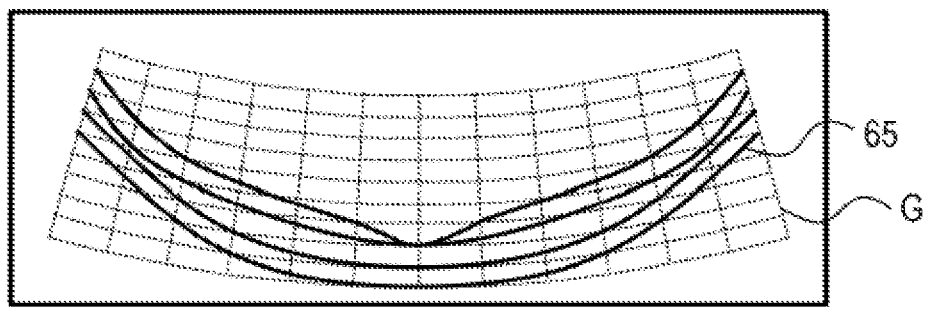
FIG. 9A is a view of a tomographic image after actual shape correction, for illustrating influence of alignment eccentricity.
Figure 9B:
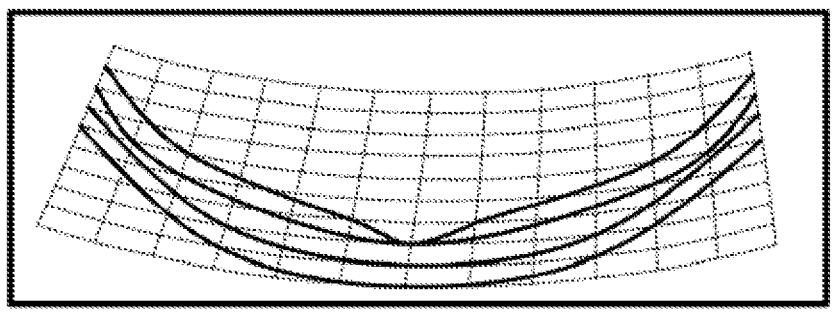
FIG. 9B is a view of a tomographic image after actual shape correction, for illustrating influence of alignment eccentricity.

FIG. 9A and FIG. 9B are each a view for illustrating influence of a difference in alignment state in a tomographic image subjected to the actual shape correction. FIG. 9A is a view for illustrating an example of a tomographic image after the actual shape correction obtained when the alignment state of the imaging apparatus 1000 is ideally matched with the optical axis of the eye E to be inspected. In this case, the actual shape of the eye E to be inspected is more accurately expressed on the tomographic image. Further, the lattice grid G corresponds to an actual locus of the measurement light. The vertical axis lines change in a radial shape, and the horizontal axis lines change in a concentric arc shape. Thus, through generation of the tomographic image having a shape close to the actual shape of the eye E to be inspected, a radius of curvature, a layer thickness, and the like of the retinal layer can be appropriately analyzed, for example, in image diagnosis.

Meanwhile, FIG. 9B is a view for illustrating an example of the tomographic image after the actual shape correction obtained when alignment eccentricity occurs. In this case, distortion is caused over the entire shape of the eye E to be inspected. In this example, for example, a significant change occurs in a curvature distribution of the fundus 65, and a curvature increases in a left region of FIG. 9B and decreases in a right region thereof. In the illustrated example, there is illustrated a change of from about 5% to about 8%. Further, distortion is similarly caused also in the lattice grid G, and in particular, the vertical axis lines are curved so as to draw an arc.

The above-mentioned change is ascribed to the following point. Specifically, the measurement light has actually an optical path in a state in which alignment eccentricity occurs as illustrated in FIG. 5B, whereas the correction processing assumes an optical path in a state in which alignment is ideally matched as illustrated in FIG. 5A. When the shape of the tomographic image is distorted as described above, for example, a difference from the actual shape is caused in analysis of a distribution of a radius of curvature regarding the shape of the retina, with the result that accurate analysis cannot be performed. Further, when a layer thickness is analyzed in the shape of the retina, length measurement is generally performed along a normal direction of the retinal layer, but accurate measurement cannot be performed due to the distortion of the shape.

(Eccentricity Correction)

In the OCT apparatus 100 in the first embodiment, in order to reduce such distortion of a tomographic image caused by alignment eccentricity, the tomographic image is subjected to eccentricity correction. The eccentricity correction in the first embodiment is now described with reference to FIG. 10A and FIG. 11B. FIG. 10A to FIG. 10D are each a view for illustrating an example of pixels of a tomographic image to be corrected by the eccentricity correction in the first embodiment. FIG. 11A and FIG. 11B are each a view for illustrating correction regarding a change in incident angle in the eccentricity correction. In FIG. 10A to FIG. 11B, the pixels of the tomographic image are expressed as 24×5 for simplicity of description. However, the pixels of the tomographic image may be suitably set in accordance with a desired configuration.

As described above, when alignment eccentricity occurs, changes in incident angle and optical path length of the measurement light with respect to the retina are caused by alignment eccentricity. Therefore, in the first embodiment, the tomographic image is corrected in accordance with the changes in incident angle and optical path length of the measurement light with respect to the retina caused by alignment eccentricity.

In the first embodiment, first, the eccentric amount acquisition unit 193 of the controller 19 acquires the alignment eccentric amount δx. The alignment eccentric amount δx can be determined by any known method. For example, the eccentric amount acquisition unit 193 may determine the alignment eccentric amount δx based on a corneal bright spot appearing on an anterior segment image, or may determine the alignment eccentric amount δx based on a pattern of the iris of the eye E to be inspected in the anterior segment image. Further, the eccentric amount acquisition unit 193 may determine the alignment eccentric amount δx based on the movement amount of the electric stage for moving the imaging apparatus 1000.

Next, the calculation unit 197 of the controller 19 determines the distance "pvl" from the pivot point to the retina based on the position of the retina in the tomographic image, the position of the reference mirror 12, and the distance (working distance) between the imaging apparatus 1000 and the eye E to be inspected as described above. After that, the calculation unit 197 determines the incident angle variation δθ of the measurement light with respect to the retina caused by alignment eccentricity based on the alignment eccentric amount δx and the distance "pvl" from the pivot point to the retina in accordance with Expression 1. The eye can be regarded as a spherical body, and hence the distance "pvl" can be set to be constant with respect to the B-scan irrespective of the angle of the scan mirror. Therefore, the incident angle variation δθ can be set to be constant with respect to one B-scan.

Further, the calculation unit 197 determines the incident angle θi of the measurement light with respect to the eye E to be inspected based on the information on the angle of the scan mirror. After that, the calculation unit 197 determines, in accordance with Expression 2, the optical path length variation δz of the measurement light caused by alignment eccentricity based on the alignment eccentric amount δx and the incident angle θi of the measurement light with respect to the eye E to be inspected. As can also be understood from Expression 2, the optical path length variation δz is different for each angle of the scan mirror. Therefore, the optical path length variation δz is determined for each A-scan included in one B-scan and used for correcting image data corresponding to the A-scan.

Figure 10A:
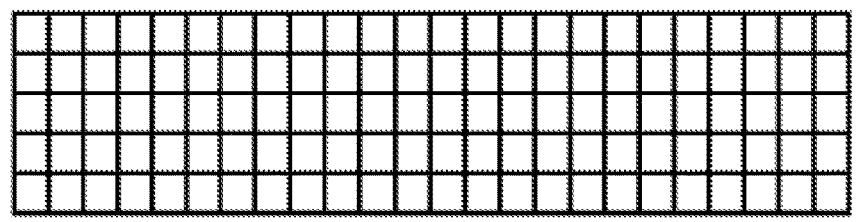
FIG. 10A is a view for illustrating eccentricity correction in the first embodiment of the present invention.
Figure 10B:
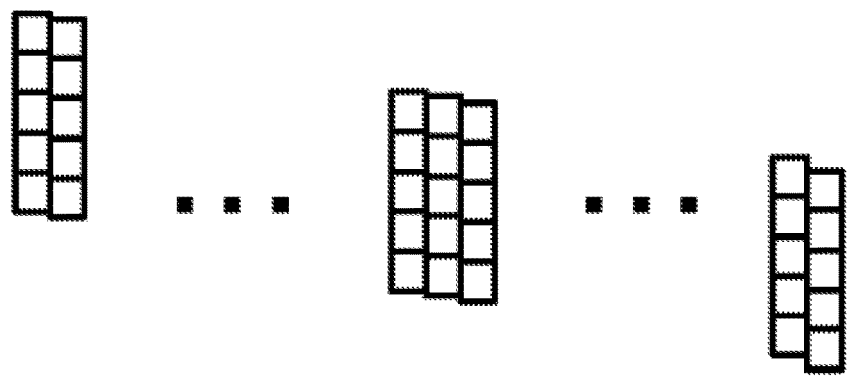
FIG. 10B is a view for illustrating eccentricity correction in the first embodiment of the present invention.
Figure 11A:
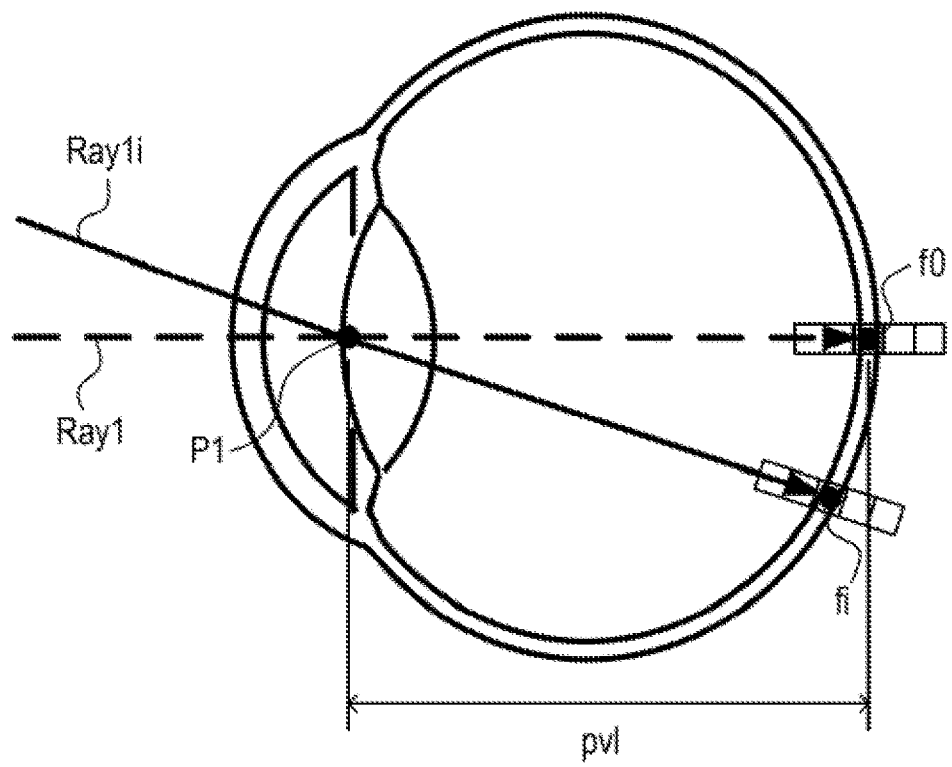
FIG. 11A is a view for illustrating eccentricity correction in the first embodiment of the present invention.
Figure 11B:
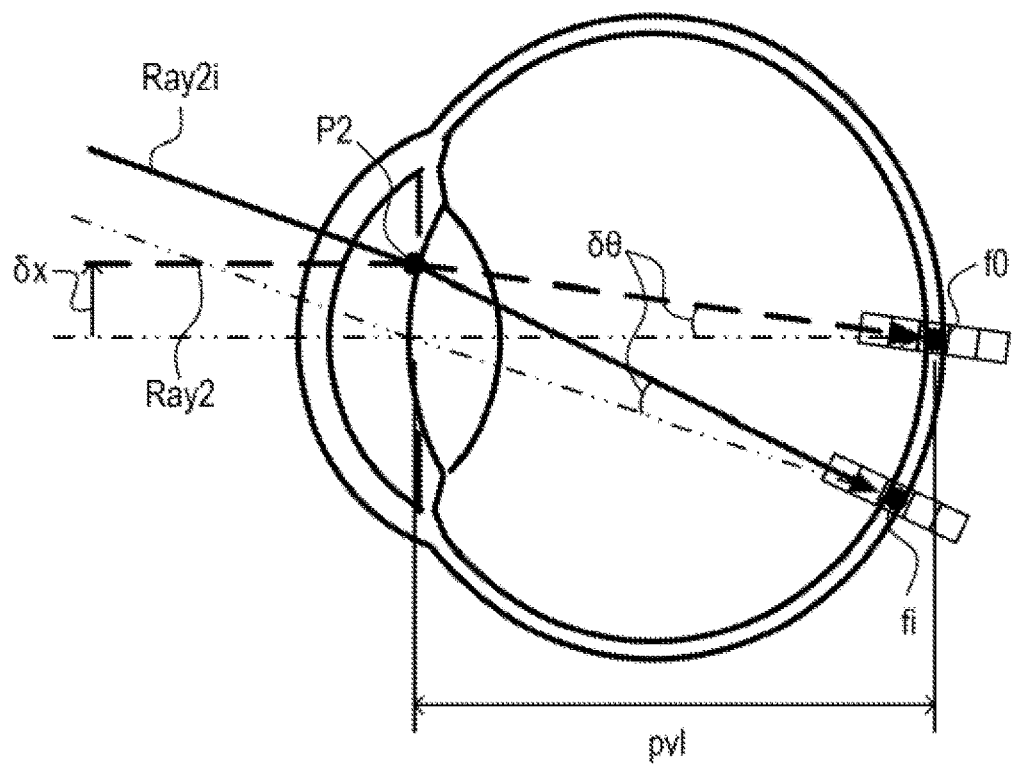
FIG. 11B is a view for illustrating eccentricity correction in the first embodiment of the present invention.

FIG. 10A is a view for illustrating an example of the pixels of the tomographic image generated based on the interference signal. In the eccentricity correction in the first embodiment, the correction unit 198 first corrects the tomographic image generated by the image generation unit 192 based on a change in optical path length of the measurement light caused by alignment eccentricity. The correction unit 198 moves a pixel position in the tomographic image corresponding to the A-scan by the measurement light at the incident angle θi with respect to the eye E to be inspected, in a depth direction of the eye E to be inspected in the tomographic image based on the optical length variation δz that is determined based on the incident angle θi. FIG. 10B is a view for schematically illustrating an example of the pixels of the tomographic image corrected based on the optical path length variation δz of the measurement light caused by alignment eccentricity.

Next, the correction unit 198 corrects the tomographic image, which has been corrected based on the optical path length variation δz, based on the incident angle variation δθ of the measurement light with respect to the fundus Ef caused by alignment eccentricity. In FIG. 11A, there are illustrated the center scanning ray Ray1 of the measurement light, the peripheral scanning ray Ray1i of the measurement light, and an imaging range to be subjected to A-scan through use of the measurement light, which are exhibited when alignment is matched. In FIG. 11B, there are illustrated the center scanning ray Ray2 of the measurement light, the peripheral scanning ray Ray2i of the measurement light, and an imaging range to F be subjected to the A-scan through use of the measurement light, which are exhibited when alignment eccentricity occurs. When the imaging ranges indicated by the rectangular frames in FIG. 11A and FIG. 11B are compared to each other, it is understood that, when a change in incident angle of the measurement light with respect to the fundus Ef is caused by alignment eccentricity, the imaging range to be scanned with each measurement light is also rotated by the incident angle variation δθ.

Figure 10C:
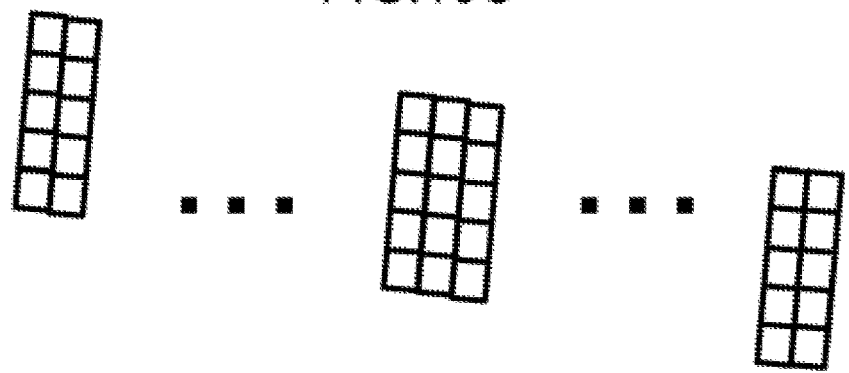
FIG. 10C is a view for illustrating eccentricity correction in the first embodiment of the present invention.

Therefore, the correction unit 198 rotates the pixel position corresponding to each A-scan of the tomographic image, which has been corrected based on the optical path length variation δz, based on the incident angle variation δθ of the measurement light with respect to the fundus Ef caused by alignment eccentricity. When the correction unit 198 rotates the pixel position corresponding to each A-scan, the correction unit 198 rotates the pixel position with the center portion in the depth direction of the pixel position corresponding to each A-scan being the center. FIG. 10C is a view for schematically illustrating an example of the pixels of the tomographic image corrected based on the incident angle variation δθ of the measurement light with respect to the fundus Ef caused by alignment eccentricity.

Figure 10D:
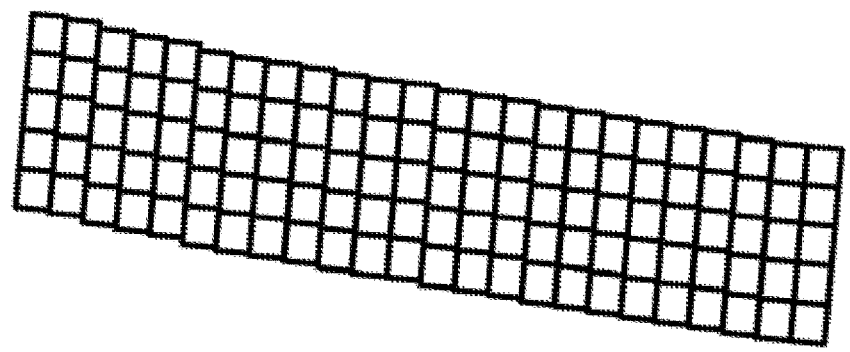
FIG. 10D is a view for illustrating eccentricity correction in the first embodiment of the present invention.

The correction unit 198 can generate a tomographic image corresponding to an actual imaging range in consideration of alignment eccentricity by performing the eccentricity correction based on the optical path length variation δz and the incident angle variation δθ. FIG. 10D is a view for illustrating an example of the pixels of the tomographic image after the eccentricity correction. With this, distortion of the tomographic image based on the optical path length variation δz and the incident angle variation δθ, which is caused by alignment eccentricity, can be reduced.

Further, distortion of the tomographic image in the actual shape correction, which is caused by alignment eccentricity, can also be reduced by subjecting the tomographic image after the eccentricity correction to the actual shape correction.

Figure 12:
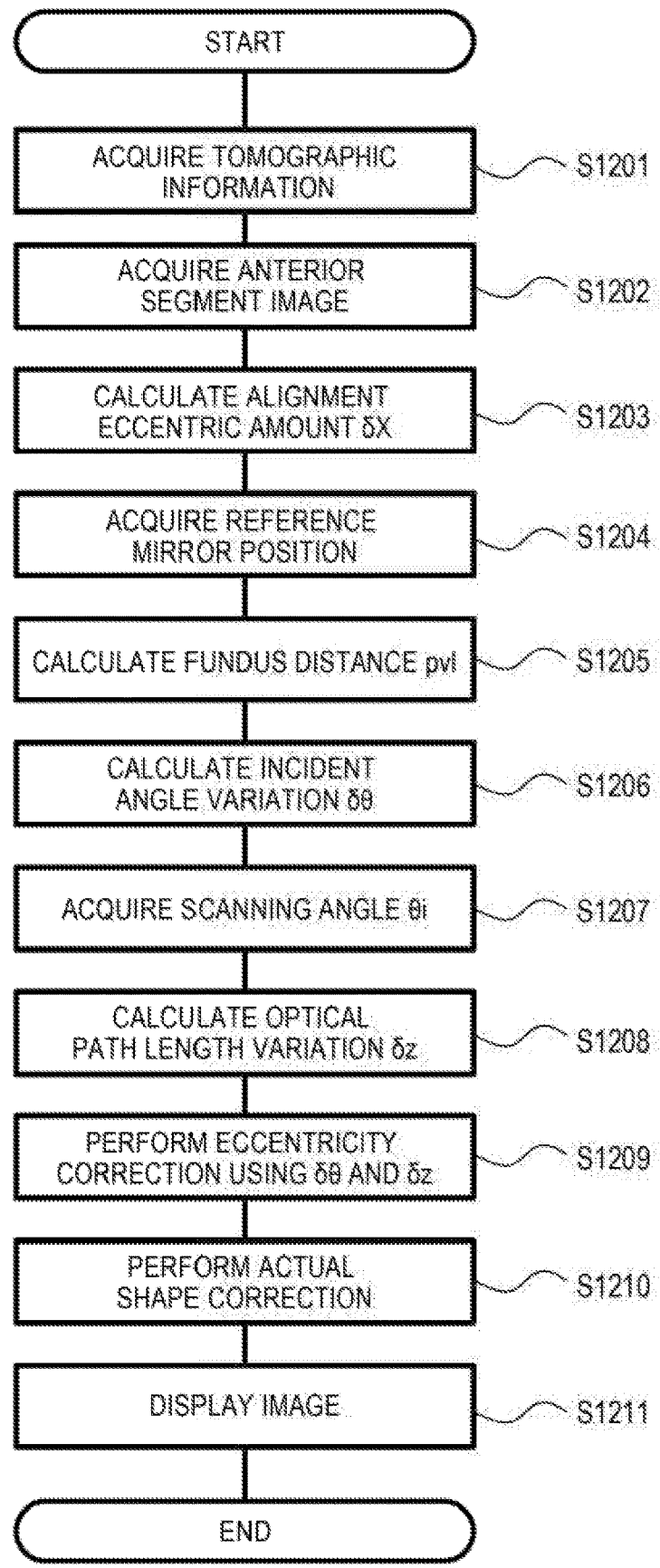
FIG. 12 is a flowchart of image generation processing in the first embodiment.

Next, processing of generating a tomographic image in the first embodiment is described with reference to FIG. 12. FIG. 12 is a flowchart of the processing of generating a tomographic image in the first embodiment.

When the processing of generating a tomographic image is started, in Step S1201, the OCT apparatus 100 performs OCT imaging under a state in which the distance (working distance) in the optical axis direction between the imaging apparatus 1000 and the eye E to be inspected is correctly aligned, and the acquisition unit 191 acquires tomographic information. Herein, the tomographic information (tomographic data) refers to information for generating a tomographic image based on the interference signal acquired by subjecting the eye E to be inspected to OCT imaging. In Step S1201, the image generation unit 192 further generates a tomographic image based on the acquired tomographic information.

In Step S1202, the imaging device 23 acquires an anterior segment image, and the image generation unit 192 generates an anterior segment image based on output from the imaging device 23 acquired by the acquisition unit 191. After that, in Step S1203, the eccentric amount acquisition unit 193 acquires the alignment eccentric amount δx from the anterior segment image.

In Step S1204, the acquisition unit 191 acquires positional information of the linear stage 13 to acquire the position of the reference mirror 12. In Step S1205, the calculation unit 197 determines the distance "pvl" from the pivot point to the fundus Ef based on the position of the reference mirror 12, the information on the position of the retina in the tomographic information, and the distance (working distance) between the imaging apparatus 1000 and the eye E to be inspected.

Next, in Step S1206, the calculation unit 127 calculates the incident angle variation δθ of the measurement light with respect to the fundus Ef by Expression 1 through use of the alignment eccentric amount δx and the distance "pvl".

In Step S1207, the calculation unit 197 determines the incident angle θi of the measurement light with respect to the eye E to be inspected during scanning through use of the angle information of the scan mirror. After that, in Step S1208, the calculation unit 197 calculates the optical path length variation δz by Expression 2 through use of the alignment eccentric amount δx and the incident angle θi.

In Step S1209, the correction unit 198 subjects the tomographic information acquired in Step S1201 to the eccentricity correction through use of the incident angle variation δθ and the optical path length variation δz. A change in incident angle corresponds to the horizontal axis in the tomographic image included in the tomographic information, and a change in optical path length corresponds to the vertical axis in the tomographic image included in the tomographic information. The correction unit 198 rearranges the pixels based on the incident angle variation δθ and the optical path length variation δz as described above, to thereby generate a tomographic image in consideration of alignment eccentricity.

In Step S1210, the correction unit 198 performs the actual shape correction on the tomographic image subjected to the eccentricity correction. As a result, even when imaging is performed under a state in which alignment eccentricity occurs, a tomographic image having a shape close to the actual shape of the eye E to be inspected can be generated.

In Step S1211, the display control unit 196 controls the display 20 so that the display 20 displays the tomographic image subjected to the eccentricity correction and the actual shape correction, and thus the processing of generating the tomographic image is ended. The operator can visually perform image diagnosis and further analyze a radius of curvature and a thickness of each layer based on the displayed tomographic image.

The processing of the eccentricity correction and the actual shape correction may be suitably controlled to be ON or OFF by the operation of the operator in accordance with the purpose of observation and analysis. Further, the display control unit 196 may cause the display 20 to display at least two of the tomographic images before and after the correction, the tomographic image subjected to only the eccentricity correction, and the tomographic image subjected to only the actual shape correction by switching. Further, the display control unit 196 may cause the display 20 to display those images in parallel. In this case, for example, the display method in the first embodiment can be associated with the related-art method of displaying a tomographic image, and there is an advantage that diagnosis can be easily performed.

As described above, the controller 19 in the first embodiment includes the acquisition unit 191 configured to acquire tomographic data of the eye E to be inspected obtained by performing optical coherence tomography imaging of the eye E to be inspected through use of the measurement light, and the eccentric amount acquisition unit 193 configured to acquire an eccentric amount of the optical axis of the measurement light with respect to the eye E to be inspected. Further, the controller 19 includes the image generation unit 192 configured to generate a tomographic image through use of the acquired tomographic data. The image generation unit 192 includes the calculation unit 197 configured to calculate the incident angle variation δθ of the measurement light and the optical path length variation δz of the measurement light with respect to the eye E to be inspected through use of the acquired eccentric amount, and the correction unit 198 configured to correct the tomographic data through use of the incident angle variation δθ and the optical path length variation δz. The tomographic data is only required be data for generating a tomographic image, and the tomographic data encompasses data on the interference signal of the eye E to be inspected, data obtained after the interference signal is subjected to Fourier transform, and data obtained by subjecting the above-mentioned data to some information processing.

More specifically, the correction unit 198 corrects the tomographic data so as to rotate the pixel position of the tomographic image in accordance with the incident angle variation δθ and to move the pixel position in the depth direction of the eye E to be inspected in accordance with the optical path length variation δz. Further, the calculation unit 197 calculates the incident angle variation δθ through use of the alignment eccentric amount δx and the distance "pvl" being the distance information in the depth direction of the eye E to be inspected in accordance with Expression 1.

Further, the calculation unit 197 calculates the optical path length variation δz through use of the alignment eccentric amount δx and the information (incident angle θi) on the scanning angle of the measurement light in accordance with Expression 2.

In the controller 19 in the first embodiment, parameters of a change in measurement light are determined based on the information on the alignment state of the eye E to be inspected, and the tomographic image is corrected through use of the determined parameters. With this, the controller 19 can generate a tomographic image having reduced distortion even under a state in which alignment eccentricity occurs.

Further, the correction unit 198 corrects the shape of the fundus Ef of the eye E to be inspected contained in the corrected tomographic data through use of the information (incident angle θi) on the scanning angle of the measurement light and the distance "pvl" being the distance information in the depth direction of the object to be inspected. Thus, the controller 19 in the first embodiment performs the actual shape correction after the eccentricity correction, to thereby enable reduction of distortion in the tomographic image after the actual shape correction, which is caused by alignment eccentricity. Therefore, the controller 19 can generate the tomographic image of the eye E to be inspected more accurately. Further, in this context, even when alignment eccentricity occurs, through use of the tomographic image subjected to the eccentricity correction and the actual shape correction, curvature distribution analysis, thickness analysis, and the like of the retinal layer can be suitably performed, for example, in image diagnosis. Those analyses can be performed by the image generation unit 192.

The curvature distribution analysis and the thickness analysis of the retinal layer may be performed by any known method. For example, in the curvature distribution analysis of the retinal layer, a radius of curvature of a position to be measured can be determined by performing fitting of three points, which are the position to be measured and A-scan positions before and after the position to be measured, with a circle with respect to an outermost surface of the fundus Ef. Further, the outermost surface of the fundus Ef may be differentiated to determine a radius of curvature. Further, regarding the thickness of the retinal layer, a thickness in a direction orthogonal to the outermost surface of the retinal layer can be determined by recognizing each layer boundary of the retina through any segmentation processing.

In the first embodiment, in the eccentricity correction, the tomographic image is corrected through use of the optical path length variation δz, and then the tomographic image is corrected through use of the incident angle variation δθ. However, the order of those corrections is not limited thereto, and the tomographic image may be corrected through use of the optical path length variation δz after the tomographic image is corrected through use of the incident angle variation δθ.

Further, in the image generation processing in the first embodiment, the incident angle variation δθ is determined through Step S1204 to Step S1206, and then the optical path length variation δz is determined through Step S1207 and Step S1208. However, the order of the processing of determining those variations is not limited thereto. For example, in order to determine the optical path length variation δz in advance, Step S1207 and Step S1208 may be performed after Step S1203, and then the incident angle variation δθ may be determined by performing Step S1204 to Step S1206.

Further, in the first embodiment, the configuration is described in which the eccentricity correction is performed on the entire tomographic image, but a site to be subjected to the eccentricity correction is not limited thereto. Only a region of interest, for example, a portion of the retina image in the tomographic image or a lesion site may be subjected to the eccentricity correction. In this case, the site to be corrected is limited, and hence the calculation amount can be reduced to shorten a processing time. Further, the site of interest in the tomographic image may be automatically specified by performing any segmentation processing, or may be specified by the operator.

Further, the image generation unit 192 may adjust the shape of the entire tomographic image to a suitable shape by adding pixels serving as blank spaces to a peripheral portion of the tomographic image after the eccentricity correction.

Further, in the first embodiment, the distance "pvl" from the pivot point to the retina surface, which corresponds to an ocular axis length, is determined based on the optical path length of the measurement light or the reference light. However, the distance "pvl" may be determined through use of a separate apparatus configured to measure an ocular axis length.

Second Embodiment

In the first embodiment, the B-scan image (two-dimensional data) acquired by scanning one line of the fundus Ef is subjected to the eccentricity correction and the actual shape correction. In this context, three-dimensional data acquired by scanning a fundus surface two-dimensionally may be subjected to the eccentricity correction and the actual shape correction. In a second embodiment of the present invention, three-dimensional data is subjected to the eccentricity correction and the actual shape correction in an OCT apparatus. Each component of the OCT apparatus in the second embodiment is the same as that of the OCT apparatus 100 in the first embodiment, and hence description of the same components is omitted through use of the same reference symbols. The OCT apparatus in the second embodiment is now described mainly regarding differences from the OCT apparatus 100 in the first embodiment.

When alignment eccentricity is corrected two-dimensionally, the same processing is performed also in the Y direction in addition to the processing in the X direction, which is described in the first embodiment. Specifically, first, the eccentric amount acquisition unit 193 calculates the alignment eccentric amounts in the X and Y directions, independently, to acquire alignment eccentric amounts δx and δy.

The incident angle variation δθ is divided into components orthogonal to each other, and those components are defined as incident angle variations δθx and δθy. In this case, the calculation unit 197 calculates the incident angle variations δθx and δθy, independently, through use of the alignment eccentric amounts δx and δy and the distance "pvl" from the pivot point to the retina by Expression 1. The distance "pvl" is common to the incident angle variations δθx and δθy.

Meanwhile, the calculation unit 197 determines the optical path length variation δz through use of the alignment eccentric amount and the measurement light incident angle in the polar coordinates system having the optical axis of the eye to be inspected as an origin. When the alignment eccentric amount in a radial direction is represented by δr, the alignment eccentric amount δr can be represented by the following expression.

$$\delta r = \sqrt{((\delta x)^2 + (\delta y)^2)} \qquad \text{(Expression 3)}$$

Further, when the incident angle in the radial direction is represented by θir, and the incident angles of the measurement light corresponding to the angles of the X-scan mirror and the Y-scan mirror are represented by θix and θiy, respectively, the incident angle θir can be represented by the following expression.

$$\theta ir=\sqrt{((\theta ix)^2+(\theta iy)^2)} \quad \text{(Expression 4)}$$

Through use of Expression 3 and Expression 4, Expression 2 can be converted into the following expression.

$$\delta z=\delta r\times\sin\theta ir \quad \text{(Expression 5)}$$

The calculation unit 197 calculates the optical path length variation δz in accordance with Expression 5.

The correction unit 198 performs the eccentricity correction in the same manner as in the first embodiment through use of the incident angle variations δθx and δθy and the optical path length variation δz. With this, the correction unit 198 can generate a three-dimensional tomographic image in consideration of alignment eccentricity. After that, the correction unit 198 performs the actual shape correction with respect to the three-dimensional tomographic image subjected to the eccentricity correction, to thereby enable generation of the three-dimensional tomographic image corresponding to the actual shape of the fundus Ef.

As described above, according to the first and second embodiments, distortion of the tomographic image caused by alignment eccentricity between the measurement light and the object to be inspected can be reduced.

In the first and second embodiments, the correction unit 198 corrects the tomographic image in the eccentricity correction and the actual shape correction. However, the correction unit 198 is only required to correct the tomographic image by correcting the tomographic data forming the tomographic image. Further, it is assumed that the tomographic image before the correction is also contained in the tomographic data for generating the tomographic image after the correction.

Further, in the first and second embodiments, the acquisition unit 191 acquires from the imaging apparatus 1000 the interference signal, the output signal from the imaging device 23, and the information on the scanning angle of the light scanner 6. However, the configuration in which the acquisition unit 191 acquires those signals is not limited thereto. For example, the acquisition unit 191 may acquire those signals from a server or an imaging apparatus connected to the controller 19 through a LAN, a WAN, the Internet, or the like.

In the first and second embodiments, a spectral-domain OCT (SD-OCT) apparatus using a superluminescent diode (SLD) as a light source is described as the OCT apparatus. However, the configuration of the OCT apparatus in one embodiment of the present invention is not limited thereto. The present invention can also be applied to any other kinds of OCT apparatus, for example, a swept-source OCT (SS-OCT) using a wavelength-sweeping light source capable of sweeping a wavelength of output light.

In the first and second embodiments, a fiber optical system using a coupler is used as a splitter. However, a spatial optical system using a collimator and a beam splitter may be used. Further, the configuration of the imaging apparatus 1000 is not limited to the above-mentioned configuration, and a part of the configuration included in the imaging apparatus 1000 may be replaced by a configuration separate from the imaging apparatus 1000.

Further, in the first and second embodiments, the configuration of a Michelson interferometer is used as an interference optical system of the OCT apparatus. However, the configuration of the interference optical system is not limited thereto. For example, the interference optical system of the OCT apparatus may have a configuration of a Mach-Zehnder interferometer.

Further, in the first and second embodiments, the case of using the fundus (retina) of the eye to be inspected as the object to be inspected is taken as an example. However, the object to be inspected is not limited thereto. An object to be inspected may be any object as long as the object to be inspected is present in a subject containing refractive elements.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-077803, filed Apr. 10, 2017, which is hereby incorporated by reference herein in its entirety.

What is claimed is:

1. An image generating apparatus, comprising:
    an acquisition unit configured to acquire tomographic data on an object to be inspected, the tomographic data being obtained by performing optical coherence tomography imaging of the object to be inspected through use of measurement light;
    an eccentric amount acquisition unit configured to acquire an eccentric amount of an optical axis of the measurement light with respect to the object to be inspected; and
    a generation unit configured to generate a tomographic image through use of the acquired tomographic data, wherein the generation unit includes:

a calculation unit configured to calculate, through use of the eccentric amount, an incident angle variation of the measurement light entering the object to be inspected, and an optical path length variation of the measurement light; and a correction unit configured to correct the tomographic data through use of the incident angle variation and the optical path length variation.

2. An image generating apparatus according to claim 1, wherein the correction unit is configured to correct the tomographic data so as to rotate a pixel position of the tomographic image in accordance with the incident angle variation and to move the pixel position of the tomographic image in a depth direction of the object to be inspected in accordance with the optical path length variation.

3. An image generating apparatus according to claim 1, wherein the calculation unit is configured to calculate the optical path length variation through use of the eccentric amount and information on a scanning angle of the measurement light.

4. An image generating apparatus according to claim 3, wherein the calculation unit is configured to calculate the optical path length variation as $\delta z = \delta x \times \sin \theta i$, where $\delta z$ represents the optical path length variation, $\delta x$ represents the eccentric amount, and $\theta i$ represents the information on the scanning angle.

5. An image generating apparatus according to claim 1, wherein the calculation unit is configured to calculate the incident angle variation through use of the eccentric amount and distance information in a depth direction of the object to be inspected.

6. An image generating apparatus according to claim 5, wherein the calculation unit is configured to calculate the incident angle variation as $\delta\theta = \delta x / pvl$, where $\delta\theta$ represents the incident angle variation, $\delta x$ represents the eccentric amount, and "pvl" represents the distance information.

7. An image generating apparatus according to claim 1, wherein the correction unit is configured to correct a shape of the object to be inspected, which is contained in the corrected tomographic data, through use of information on a scanning angle of the measurement light and distance information in a depth direction of the object to be inspected.

8. An image generating apparatus according to claim 7, wherein the generation unit is configured to subject the tomographic data containing the corrected shape of the object to be inspected to analysis of a curvature distribution of the object to be inspected.

9. An image generating apparatus according to claim 7, wherein the generation unit is configured to subject the tomographic data containing the corrected shape of the object to be inspected to analysis of a thickness of a layer of the object to be inspected.

10. An image generating apparatus according to claim 7, further comprising a display control unit configured to cause a display to display the tomographic image,
wherein the display control unit is configured to cause the display to display, by switching or in parallel, at least two of tomographic images using the tomographic data before and after being corrected by the correction unit and tomographic images using the tomographic data after the shape of the object to be inspected, which is contained in the tomographic data before and after being corrected by the correction unit, is corrected through use of the information on the scanning angle and the distance information.

11. An image generating apparatus according to claim 1, wherein the object to be inspected includes a fundus of an eye to be inspected, and
wherein the eccentric amount acquisition unit is configured to acquire the eccentric amount through use of an anterior segment image of the eye to be inspected.

12. An image generating apparatus according to claim 1, wherein image generating apparatus is connected to an imaging apparatus configured to perform optical coherence tomography imaging of the object to be inspected, and
wherein image generating apparatus further comprises a positioning unit configured to position the imaging apparatus with respect to the object to be inspected.

13. An image generating apparatus according to claim 1, wherein the correction unit is configured to correct any one of two-dimensional data and three-dimensional data as the tomographic data.

14. An image generating method, comprising:
acquiring tomographic data on an object to be inspected, the tomographic data being obtained by performing optical coherence tomography imaging of the object to be inspected through use of measurement light;
acquiring an eccentric amount of an optical axis of the measurement light with respect to the object to be inspected; and
generating a tomographic image through use of the acquired tomographic data,
wherein the generating a tomographic image includes:
calculating, through use of the eccentric amount, an incident angle variation of the measurement light entering the object to be inspected, and an optical path length variation of the measurement light; and
correcting the tomographic data through use of the incident angle variation and the optical path length variation.

15. A non-transitory computer-readable medium having stored thereon a program for causing, when being executed by a processor, the processor to perform each step of the image generating method of claim 14.

* * * * *